United States Patent [19]

Bonner

[11] 4,292,589
[45] Sep. 29, 1981

[54] EDDY CURRENT METHOD AND APPARATUS FOR INSPECTING FERROMAGNETIC TUBULAR MEMBERS

[75] Inventor: Stephen D. Bonner, Houston, Tex.

[73] Assignee: Schlumberger Technology Corporation, Houston, Tex.

[21] Appl. No.: 37,423

[22] Filed: May 9, 1979

[51] Int. Cl.³ .................... G01N 27/72; G01N 27/82; G01R 33/12

[52] U.S. Cl. .................................. 324/221; 324/233; 324/241

[58] Field of Search .............................. 324/219–221, 324/225, 234, 236–243, 233; 340/199, 870.25, 870.31, 870.15; 336/170, 215

[56] References Cited

U.S. PATENT DOCUMENTS

| | | |
|---|---|---|
| 2,992,390 | 7/1961 | DeWitte . |
| 3,317,824 | 5/1967 | Wood . |
| 3,405,354 | 10/1968 | Callan et al. .......................... 324/233 |
| 3,437,810 | 4/1969 | Wood et al. .......................... 324/221 |
| 3,449,662 | 6/1969 | Wood . |
| 3,465,274 | 9/1969 | Proctor . |
| 3,504,276 | 3/1970 | Proctor et al. . |
| 3,543,144 | 11/1970 | Walters et al. . |
| 3,940,689 | 2/1976 | Johnson, Jr. . |
| 4,016,519 | 4/1977 | Haas . |

Primary Examiner—Gerard R. Strecker
Assistant Examiner—Walter E. Snow

[57] ABSTRACT

Casing inspection apparatus and method are disclosed for determining defects and other anomalies in ferromagnetic oil well casing. The inspection apparatus utilizes a pair of coaxial transmitter coils for generating an alternating magnetic field in the casing thereby inducing circumferential currents in the casing wall. These circumferential currents and the magnetic field associated with the currents are perturbed by corrosion, holes, and other anomalies both inside and outside the casing wall. Differential receiver coils are urged in proximity with the casing wall to generate a differential receiver signal in response to such perturbations in the magnetic field. The differential receivers are provided with three coils serially connected and having N, 2N and N winding turns respectively. The windings of the coils are disposed in adjacent relationship to one another and wound in a direction opposite to the adjacent winding. The casing inspection apparatus achieves enhanced sensitivity to small defects and reduced sensitivity to magnetic anomalies by processing both the amplitude and phase components of the receiver signal.

32 Claims, 16 Drawing Figures

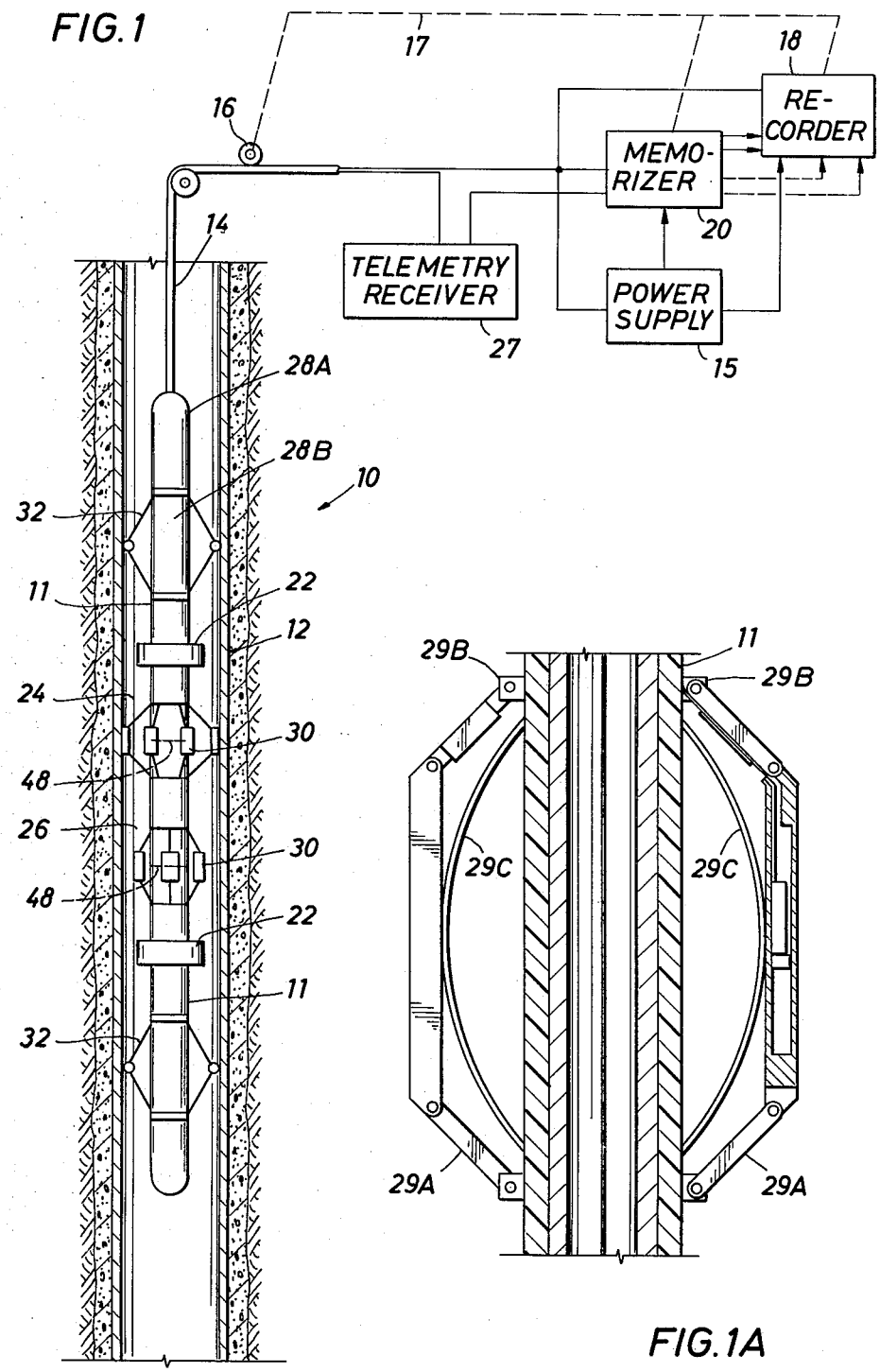

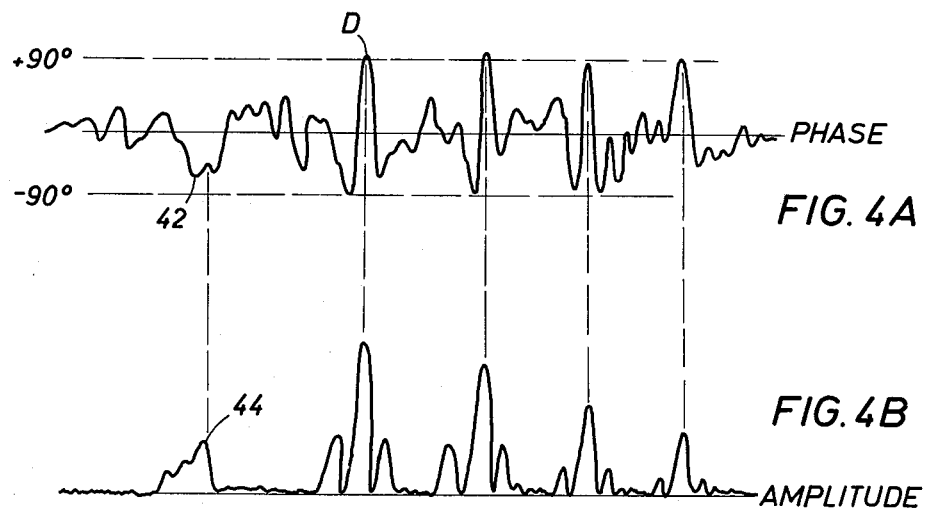
FIG. 4A
FIG. 4B
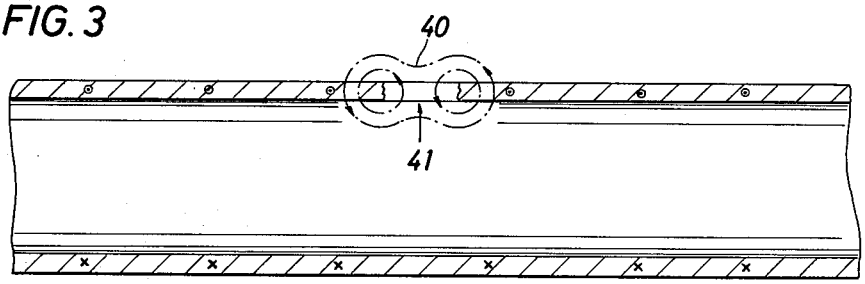
FIG. 3
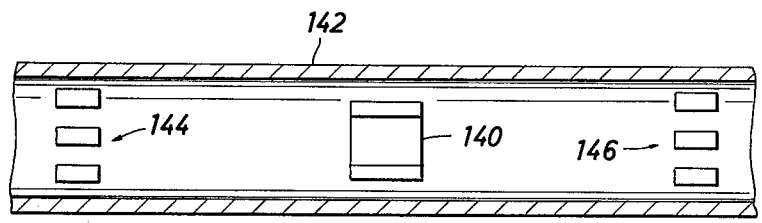
FIG. 11A
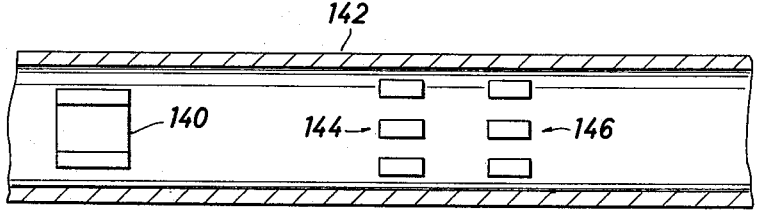
FIG. 11B

EDDY CURRENT METHOD AND APPARATUS FOR INSPECTING FERROMAGNETIC TUBULAR MEMBERS

BACKGROUND OF THE INVENTION

The invention relates to an apparatus and method for discovering the location and severity of defects in ferromagnetic oil well casings. More specifically the invention relates to a casing inspection system and method utilizing eddy current principles for determining small defects and other anomalies in oil well casings.

In the oil and gas industry buried pipe is used extensively for transporting hydrocarbon products. Since the exteriors of these casings are not readily accessible for discovering corrosion or other aging factors, it is necessary to inspect the pipe from its interior. Continuing maintenance of the casing by periodic interior inspections reduces emergency repairs, prevents unexpected shutdowns, allows scheduled replacement of unsound casing, and enhances the general overall efficiency of the transport operation.

It is common to inspect the overall soundness of oil well casings and other ferromagnetic material by generating a magnetic field within the member to be inspected. There are many casing parameters that may be probed during such inspections. For example, some inspection devices determine the overall thickness of the casing. Other devices are designed to detect small defects such as pits, holes, cracks and other localized anomalies in the casing. Still other devices are designed to determine whether any given defect is on the internal or external wall of the casing. In order to more accurately determine the soundness of the casing or piping, many existing devices incorporate means for determining combinations of the above referenced parameters.

Casing inspection tools and methods exist utilizing d.c. flux to energize an oil well casing to determine the location of defects therein. Such a device is disclosed in U.S. Pat. No. 3,940,689 which structurally comprises a central d.c. electromagnet with two end pole pieces for producing a magnetic field within the casing, and a pair of receiver arrays disposed between the end pole pieces for detecting discontinuities within the casing walls. In this type of device, utilizing flux leakage measurements, sections of the casing wall being inspected are magnetized with d.c. magnetic flux.

It is known that in an unflawed casing section the casing magnetic flux flows longitudinally in a uniform method. It is also known that a hole in the casing causes a local increase in the magnetic reluctance of the casing. This in turn disturbs the longitudinal flux pattern and thus flux lines bulge from the walls of the casing. This bulging flux or fringing flux is the flux leakage detected by receiver coils located adjacent to the casing wall. Sets of two receiver coils, displaced axially and being flat wound or printed circuits, are used to detect fringing flux about a discontinuity in the differentially casing wall. The d.c. flux produced by the electromagnets normally has a magnitude on the order of 20 gauss. Since the magnetic field has such a large intensity, the receiver coils may comprise a low number of winding turns, on the order of 15 per coil. This requirement of 15 winding turns readily enables the use of the printed circuit coils or flat wound receiver coils.

A major disadvantage in the casing inspection device energized by a d.c. source to discover discontinuities by a magnetic flux fringing in the casing is that the larger the casing the larger the size of the magnetic core required to properly magnetize the casing. Thus, with the increase in size of the magnetic core the casing inspection tool itself becomes proportionally heavier.

U.S. Pat. No. 3,940,689 further discloses a means for detecting whether the casing defect is interior or exterior to the casing wall. This determination is made by using localized eddy current measurements which are sensitive only to inner wall casing defects, since the eddy current penetration is only about one millimeter into the skin of the casing wall. In order to effectively induce the eddy currents in a localized region of the casing wall a second transmitter coil is located parallel to the casing wall and energized to generate a high frequency alternating magnetic field.

The second transmitter coil generating the high frequency alternating magnetic field is disclosed in U.S. Pat. No. 3,940,689 as being disposed within the receiver pad along with the receiver coils. Since a printed circuit coil is utilized in making the flux leakage measurement, placement and alignment of the second receiver coil in the receiver pad in such a manner so as to have the receiver coil measure the high frequency field causes increased manufacturing difficulties.

Measurements of thickness and local pitting of oil well casings are also made using alternating magnetic fields. U.S. Pat. No. 2,992,390, discloses an inspection tool utilizing a magnetic core element having a transmitter coil located thereon. The transmitter coil is driven by an alternating current source and generates an alternating magnetic field in the casing. The magnetic core is laminated to prevent eddy currents from flowing therein. Receiver coils are placed predetermined distances from the transmitter coil to determine general thickness variations, local, pitting, and permeability changes by measuring the energy received at their specific location. The receiver coils are wound about stubs or protrusions from the magnetic core, with each stub located a fixed distance from the transmitter depending upon the parameter to be measured.

Prior d.c. magnetic flux leakage casing measurement tools have a major disadvantage because of their inability to distinguish magnetic anomalies from the real casing defects. Further, the overall weight of these devices may be excessive due to the need for an electromagnetic core. Prior eddy current casing measurement tools have relied on magnetic central cores and multiple frequency excitation with resultant heavy and complicated equipment.

Also, use of flat wound or planar configuration printed circuit coils as receiver coils presents the disadvantage of requiring a magnetic field having a magnitude on the order of 20 gauss due to the limited number of windings per coil.

SUMMARY OF THE INVENTION

The casing inspection apparatus and method of the invention detects real anomalies in oil well casings while being relatively insensitive to magnetic anomalies or inherent material differences of the casing. Further, the overall weight of the tool is reduced because utilization of a heavy electromagnet to generate d.c. magnetic flux is obviated.

The casing inspection tool according to the invention has a primary objective of discovering localized defects and a secondary objective of distinguishing magnetic anomalies by evaluating the phase and amplitude components of a single frequency output voltage signal in a differential receiver. A unique differential receiver of the invention comprises three serially connected coils having N, 2 N, and N windings, respectively. Each receiver coil winding is wound in a direction opposite to that of the adjacent winding.

According to one form of the invention, the casing inspection tool includes at least one coaxial transmitter coil positioned in the casing and excited by an alternating current source so as to generate an alternating magnetic field within the casing. The alternating magnetic field induces circumferential currents in the casing. An array of new and improved differential receiver coils is further provided to detect any signal perturbations in the currents caused by holes, pits, etc. in the casing which are associated with the circumferential currents. Signal processing circuitry is coupled to the receiver coils to measure the amplitude and phase components of the magnetic field associated with the currents in order to detect actual defects in the casing while distinguishing magnetic anomalies.

In a preferred embodiment, two coaxial transmitter coils are utilized to generate the alternating magnetic field within the casing. A first and second array of differential receiver coils, adapted to be set in a carrying member moveable along the inside of the casing, are located a predetermined distance between the transmitter coils. An alternative configuration according to the present invention includes a coaxial transmitter coil centered between a first and a second array of differential receiver coils. Another alternative configuration of the transmitter-receiver arrangement includes a single coaxial transmitter axially spaced from a first and second array of differential receiver coils, where the first and second arrays are adjacent to one another. In all arrangements of the transmitter coil(s) with the receiver arrays, the transmitter coil(s) is preferably driven by an alternating current source having a frequency in the range of 30–40 Hz.

An outstanding feature of the instant invention is the coil arrangement of the differential receiver. In a preferred embodiment, the differential receiver comprises a carrying member supporting three coils. Although having three physical coils, the receiver is electrically equivalent to a differential coil pair. The first coil has N windings arranged around a bobbin disposed within the carrying member. The second coil has 2 N windings serially connected to the windings of the first coil and wound around a bobbin in a direction opposite to the windings of the first coil. A third coil is provided having N windings serially connected to the windings of the second coil and wound around the bobbin in a direction opposite to that of the windings of the second coil. This coil arrangement which is electrically equivalent to a differential coil pair, is passed in sliding engagement with the interior side of the casing wall and provides a voltage output signal in response to a perturbed magnetic field associated with the circumferential currents. An alternative arrangement of the three receiver coils is that all three coils are wound in the same direction but electrically connected to provide an equivalent differential coil pair.

Utilization of a bobbin structure for supporting the windings of the receiver coil facilitates providing increased numbers of winding turns and uniformity of coil shape, size and spacing for multiple coils. This feature also ovecomes the disadvantage of the planar coil arrangement and its requirement of a large magnitude magnetic field.

In a preferred embodiment, a reference receiver is provided and located behind each receiver coil array in the center of the casing. The reference receiver provides a reference signal indicative of the magnetic field in the center of the casing. Signal processing circuitry is utilized to measure the amplitude of the voltage signal received from the differential receiver arrays along the interior of the casing wall. The difference in phase of the voltage signal from the differential receivers along the interior wall is measured with respect to the phase of the signal received from the reference receiver located in the center of the casing. Both the voltage amplitude difference and phase difference signals are proportional to the effective volume of the anomaly.

For determining whether the defect is on the interior surface of the casing, a second localized transmitter coil is provided parallel to the casing wall, for generating a second alternating magnetic field. The differential receivers used to detect the magnetic field generated by the coaxial transmitter are also utilized to detect perturbations in the localized eddy currents generated by the second alternating magnetic field. The signal processing circuitry provides means for differentiating the signal induced by the parallel transmitter coil which is driven at a higher frequency, on the order of 2 KHz.

A general object of the invention is to provide a new and improved casing inspection apparatus utilizing low frequency eddy current techniques.

BRIEF DESCRIPTION OF THE DRAWINGS

The features and advantages of the invention will become more apparent upon reading the following detailed description in reference to the drawings in which:

FIG. 1 is a schematic view of a preferred embodiment of the casing inspection apparatus in accordance with the principles of the invention;

FIG. 1A is an expanded view of the receiver array of FIG. 1;

FIG. 3 is a schematic representation of a perturbated magnetic field at a defect in an oil well casing;

FIGS. 4A and 4B are graphic representations of the phase and the amplitude of the voltage signal delivered from the receiver pad;

FIGS. 11A and 11B illustrate alternative embodiments of the transmitting and receiver coil arrangements according to the invention.

DESCRIPTION OF THE INVENTION

Figure 2A:
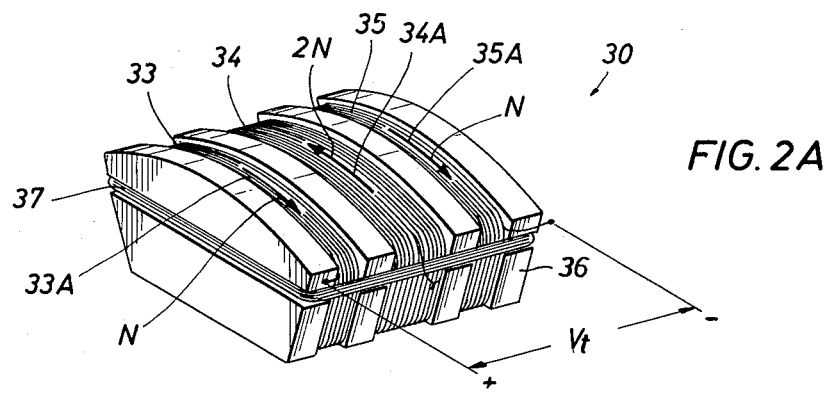
FIG. 2A is an illustrated view of a preferred embodiment of the unique effective differential coil arrangement of the invention.

In FIG. 1, a preferred embodiment of a casing inspection tool 10 is shown disposed in an oil well casing 12 according to normal operation of the tool. The tool 10 is utilized to inspect the casing 12, typically a liner for oil or gas wells, for flaws such as pitting or cracking. The casing inspection tool 10 is normally suspended from a logging cable or wireline 14. Use of the wireline 14 enables movement of the casing inspection tool 10 throughout the length of the casing 12. The wireline 14 also provides conductors for signal transmission between the tool 10 and surface equipment where the signals are recorded and evaluated. In addition, the wireline 14 provides power via a surface power supply 15 to the inspection tool 10 and its complementary circuitry.

In order to coordinate the recorded measurements made by the casing inspection tool 10 with the depth of the tool at the measuring site in the casing 12, a measuring wheel 16 is arranged to be driven by movement of the cable 14 onto and off of the cable winch which is cooperatively coupled, as by a pulse generator or suitable mechanical linkage 17, to a recorder 18 for producing records thereon which are a function of the depth of the tool 10. Since it is generally preferred that the several logging records provided by the recorder 18 are all presented with a common depth scale, the circuitry uphole is arranged also to include a "depth memorizer" 20, which is driven by the measuring wheel 16 for momentarily storing one set of data signals from the tool 10 for simultaneous presentation on the recorder with one or more other sets of data signals from the tool 10. Suitable memorizer circuits are shown in U.S. Pat. No. 3,166,709 and U.S. Pat. No. 3,405,349 which are incorporated by reference herein.

In the preferred embodiment of the invention, the casing inspection tool 10 is provided with a pair of coaxial transmitters 22 suspended from an elongated body 11. The elongated body or mandrel 11 is largely non-magnetic, and non-conductive and may be fabricated out of fiberglass material with metal reinforcing such that there are no conductive paths.

The coaxial transmitters 22 suspended from the wireline 14 are electrically driven by the a.c. power source 15 via a conductor in the wireline 14 at a frequency in the range of 30 to 40 hertz. Unlike prior inspection tools relying on flux leakage measurements of d.c. magnetic flux, the tool 10 according to the invention relies on the generation of alternating current flux, which obviates the need for a heavy iron core providing low reluctance flux data.

The coaxial transmitters 22 are disposed a predetermined distance away from one another and have first and second arrays of receiver pads 24 and 26 located therebetween also suspended from elongated body 11. A cartridge 28A is provided to house circuitry, shown in the block diagram of FIG. 5 and described below, for evaluating the phase and amplitude of the voltage signal detected at each receiver pad 30 on arrays 24 and 26. A cartridge 28B is provided to house digital telemetry circuitry, described below, for delivering a phase-amplitude signal product to the uphole telemetry receiver 27 shown in FIG. 1. Centralizers 32 operate with the elongated body 11 to center the tool 10 within the casing 12.

The transmitter coils 22 shown in FIG. 1 are spaced a predetermined distance from each of the receiver arrays 24 and 26 such that the spacing is small enough that reasonable signal levels are obtained in the receiver coils, but large enough so that the direct mutual coupling from the transmitters does not dominate the signal due to the defect.

Where the outside diameter of the casing 12 is 7.5" or less, the transmitters 22 and receiver arrays 24 and 26 may preferably be spaced 17.5" on center. Casings having an outside diameter greater than 7.5" may have transmitters 22 and receiver arrays 24 and 26 spaced 21" on center.

The casing inspection tool 10 is provided with twelve receiver pads 30 disposed in two arrays 24 and 26 between coaxial transmitters 22, arranged relative to one another in a manner to provide a full 360° inspection of the inside surface of the casing 12. As depicted in FIG. 1, this complete circumferential coverage is best accomplished by dividing several inspection receivers and symmetrically arranging half of these at equal intervals around one portion of the body 11, arranging the remaining receiver coils 30 at a second portion of the body 11. By angularly offsetting the receiver pads of array 24 in relation to the receiver pads of array 26, each of the pads in array 26 will be respectively examining a narrow longitudinal strip of the casing 12 which lies between the slightly overlapped two adjacent strips of the casing that are being examined by the inspection receiver coils immediately thereabove. As the new and improved inspection tool 10 is moved through the casing 12, the upper inspection receiver array 24 will be continuously examining a number of circumferentially spaced bands or longitudinal strips along the casing wall having gaps therebetween and the lower array 26 will be continuously examining these gaps to assure a complete survey of the casing wall 12.

FIG. 1A illustrates a mechanical arrangement that may be employed to maintain the receiver pads 30 in arrays 24 and 26 in operative engagement with the inner wall of the casing 12. For example, several receiver coils 30 could be mounted onto the tool body 11 in keeping with the principles of U.S. Pat. No. 2,736,967. As shown in FIG. 1A, however, the preferred embodiment of the present invention locates the receiver array such that the receiver coils 30 are pivotally coupled to the outer ends of rigid arms 29a which in turn have their inner ends pivotally coupled to longitudinally-spaced collars 29B slidably mounted around the tool body 11. Springs 29C are arranged for urging the receiver coils into sliding engagement with the wall of the casing 12.

A unique coil arrangement of the receiver pads 30 illustrated in FIG. 2A is provided, according to this invention, as part of the casing inspection tool 10. Each receiver pad 30 includes three individual coils 33, 34 and 35 having N, 2 N and N turns respectively. The coils 33, 34 and 35 are wound on a bobbin core 36 adjacent to one another. Although the coils 33, 34 and 35 are connected in series to one another, adjacent coils may be wound in opposing directions to form an effective differential coil arrangement. As shown in FIG. 2A by arrow 33A and arrow 34A, adjacent coils 33 and 34 are wound in opposite directions. Coil 35 is wound in a direction opposite to coil 34 as indicated by arrow 34A and arrow 35A. This arrangement provides a differential measurement of the change in flux of a magnetic field generated by the coaxial transmitters 22 within the casing 12.

Figure 2B:
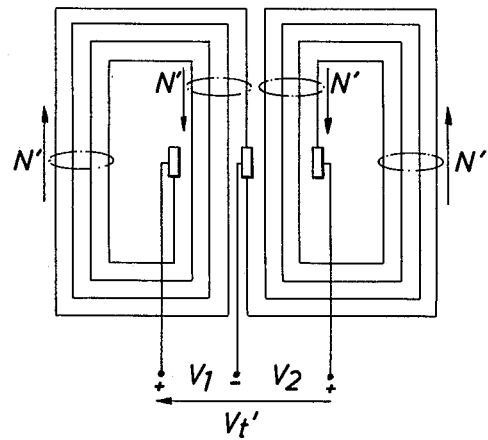
FIG. 2B is an illustrated view of a planar configuration differential coil pair as identified in the prior art.

FIG. 2B illustrates a planar, differential printed circuit coil found in the prior art.

The three coil arrangement on a bobbin structure of the present invention as illustrated in FIG. 2A is electrically equivalent to the prior art flat coil arrangement of FIG. 2B, when used to sense the presence of flux perturbations extending a short distance from a ferromagnetic casing. The voltage $V_t$ between ends of coils 33 and 35 yield a measurement electrically equivalent to the voltage $V_t'$ of the flat coil arrangement of FIG. 2B for an equal number of turns. The equivalence can be understood by recognizing that the flat coil arrangement of FIG. 2B has N' turns for conducting current in the positive direction on the left hand side of the coil arrangement, 2N' turns for conducting current in the negative direction in the middle part of the arrangement, and N' turns for conducting current in the positive direction on the right hand side of the coil arrangement. Electrically, the voltages $V_1$ and $V_2$ of FIG. 2B are subtracted to yield a voltage $V_t$ as illustrated which is a measurement of the flux difference linking the two coils. The planar configuration coil in FIG. 2B has the inherent limitation of accepting a small number of winding turns whereas the three coil arrangement of the present invention (as illustrated in FIG. 2A), having a bobbin core, will accept on the order of 1,500 to 2,000 windings. This increase in the number of windings per coil facilitates the detection of a magnetic field of extremely small magnitudes, e.g., on the order of 200$\mu$ gauss.

Again referring to FIG. 1, the transmitters 22 are driven by the alternating current source 15 to generate an alternating magnetic field within and around the casing 12. The effect of the alternating magnetic field is to induce circumferential currents in the casing wall. When there is a casing anomaly in the form of a pit or crack, the current splits and flows around the sides of that anomaly (analogous to a stream of water flowing around a rock or piling). This deformation in the flow of the circumferential current gives rise to a perturbation in the magnetic field confined to the vicinity of the defect.

The magnetic field around the defect can be considered as the superposition sum of two magnetic fields. The first part of the sum is the magnetic field that would be present at the location of the defect if there were no defect, called the nominal field. The second part of the sum is the perturbation field due solely to the deformation of the circumferential current around the defect, such as the perturbation field 40 illustrated in FIG. 3. The magnitude of this perturbation field 40 is proportional to the axial length and depth of penetration of the defect or corrosion 41. An important aspect of the perturbation field 40 is the phase difference between it and the nominal field. If one moves in the axial direction a distance from the transmitter 22 far enough so that the magnetic field lines passing through a plane perpendicular to the casing axis at that point pass through the casing wall twice, the circumferential current flowing in the casing wall will lag the nominal field by 90°. The perturbation B field 40 has the same phase as the circumferential current since it totally depends on the deformation of the circumferential current. Hence, when the perturbation field 40 around the defect 41 is about the same strength as the nominal field or stronger, and the receiver pad 30 is drawn across the defect 41 at a uniform speed, a phase modulation as well as an amplitude modulation of the alternating receiver voltage will occur.

FIG. 4A shows phase and amplitude waveforms produced by the apparatus of the invention. If the perturbation field 40 (FIG. 3) is dominant so that the nominal field is negligible, as the receiver pad 30 is moved across the defect 41, the phase of the alternating receiver voltage will change from (e.g., see the waveform at "D" of FIG. 4A) 0° to −90°, through 0° to +90°, then to −90°, and back to 0°, the positive and negative phase changes due to the differential connection of the coils in receiver pad 30. Any increase in the volume of the defect 41 will not change this characteristic phase modulation once the perturbation field 40 is dominant. However, the amplitude of the differential waveform from the apparatus of the invention is proportional to the effective volume of the casing anomaly. For defects which are larger in the axial direction than they are in the circumferential direction, the effective volume is roughly found by taking the axial extent of the pit or crack and using it as the diameter for a circular defect with the same depth of wall penetration as the actual defect. For defects that are longer in the circumferential direction than they are in the axial direction, the effective volume is roughly the same as the actual volume. Amplitude waveforms from the apparatus of the invention are shown in FIG. 4B.

For some magnetic anomalies (abrupt changes in magnetic properties confined to a small area on the order of the face size, the receiver coil), it has been discovered that the phase modulation characteristic is different from that of an actual defect. When the perturbation field around the magnetic anomaly is dominant or even on the same order as the nominal field, the phase modulation of the alternating receiver voltage changes from 0° (over nominal casing) towards −90°, and then back to 0° again. The amplitude of the alternating receiver voltage is proportional to the severity of the magnetic anomaly, but when compared to actual defects, the amplitude response can be considered relatively insensitive to magnetic anomalies. This effect is illustrated in FIGS. 4A and 4B at points 42 and 44 where the amplitude response 44 is small and the phase response 42 is negative. Thus, the advantages of the present system are: (1) the phase characteristic of a magnetic anomaly is different from that of a real defect; and (2) the amplitude response to a magnetic anomaly is relatively small compared to actual defects.

Therefore, a non-ambiguous determination of casing integrity can be made based upon the dependence of the phase modulation on the presence of an anomaly and the proportional dependence of the amplitude modulation of the alternating receiver voltage on the volume of the anomaly.

By looking at the typical phase and amplitude waveforms shown in FIGS. 4A and 4B, it should be apparent that one could multiply the two waveforms, point by point, without loss of information. The advantages of multiplying the waveforms are twofold.

First, if no defects are present under the receiver pad 30, the amplitude is very small and multiplying the amplitude-phase in this situation will remove most of the "noise" present in the phase curve. This "noise" is due to the fact that the magnetic properties vary slightly from inch to inch. It will take a severe change in magnetic properties to give rise to a magnetic anomaly. These minor variations are generally not considered as magnetic anomalies.

The second advantage is that because the phase modulation characteristic of a magnetic anomaly and a defect are different, multiplying the two waveforms over a real defect gives a "bipolar" waveform, whereas over a magnetic anomaly, the product waveform is essentially one-sided. The phase signal becomes important only when there is an increase in the amplitude of the 35 Hz receiver voltage. Thus multiplication of the waveform reduces the data rate necessary to transmit all the information, and it also simplifies the display problems by reducing the number of waveforms to be displayed.

Detection of the phase modulation may be accomplished by using an FM discriminator. However, a more convenient method in accordance with the present invention involves the use of a reference receiver coil 48 or pair of coils connected differentially, concentric with the tool 10 axis located directly underneath the receiver pad 30 as described above (see FIG. 1). Additionally, the amplitude and/or phase relative to the transmitter current of the signal received by such a receiver pad 30 may be used to normalize the individual responses from the pad receivers so that the log would display the percentage of wall thickness reduction.

Figure 5:
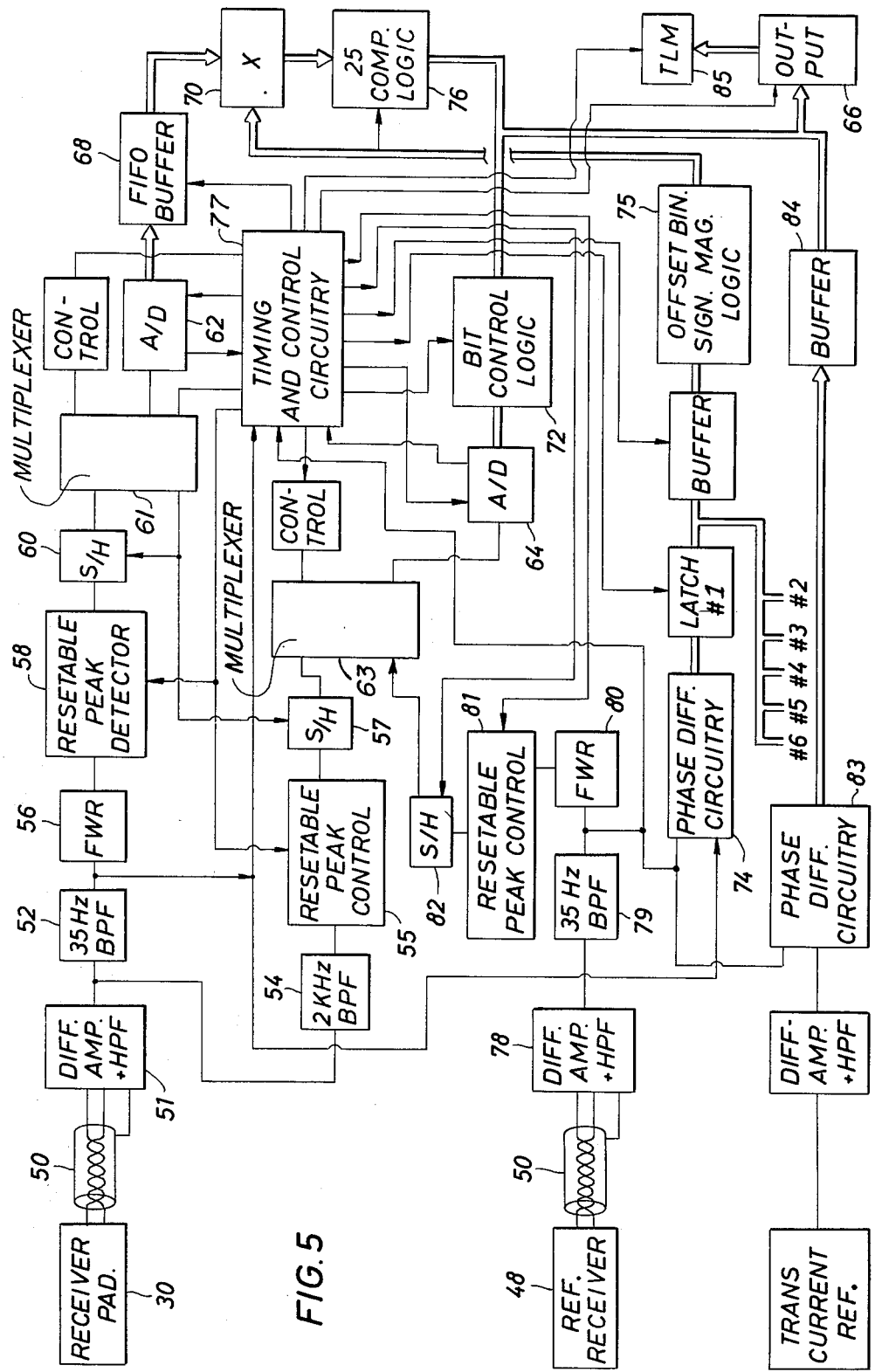
FIG. 5 is a block diagram of the electronic circuitry used to measure phase and amplitude of the voltage signal delivered in accordance with one embodiment of the invention.

Another feature of the present invention includes electronic signal processing circuitry connected to the receiver pads 30, as shown in FIG. 5.

The signal processing circuitry used to analyze the voltage signal obtained from each of the receiver pads 30 is placed in a cartridge such as the cartridge 28A shown in FIG. 1. The voltage signal generated by moving the receiver pad 30 over the casing 12 indicates that either a real anomaly exists in the casing or merely a magnetic anomaly exists. A magnetic anomaly is an inherent material fault in the casing characterized by displaying magnetic properties different from those of the rest of the casing material.

The signal of each receiver pad 30 is fed via shielded, twisted cable 50 into a circuit having a differential amplifier 51 with a second order high pass characteristic. The output of this amplifier 51 is fed into two different bandpass filters 52 and 54. One bandpass filter 52 has a fourth order characteristic with center frequency equal to that of the low frequency transmitter 22 (30–40 Hz).

The other bandpass filter 54 has a second order characteristic with a center frequency of 2 kHz. The 2 kHz frequency is that frequency at which a localized eddy current transmitter 37 will operate as shown in FIG. 2A, located orthogonally to the receiver coil. This transmitter coil 37 is used for discrimination between inside and outside defects. The orthogonal transmitter coil 37 induces eddy currents in the casing 12 in a plane parallel to that of the coil. The eddy current flow produces a second magnetic field which opposes the excitation field induced by the coaxial transmitters 22. The resultant magnetic field is the vector sum of the high and low frequency excitation fields. Thus, when the receiver pad 30 having a second transmitter coil 37 wound therein moves along the inside wall of the casing, and the defect is on the inner wall, the flow of the high frequency eddy currents are impeded, causing the second magnetic field to be perturbated. This perturbated magnetic field is detected by the effective coil pair due to the imbalance of the field being measured. This imbalance creates an increase in the 2 kHz voltage signal output from the coil pair. Use of the 2 kHz localized eddy current technique is a standard method in the art for determining inside wall defects. The use of this eddy current technique is illustrated in U.S. Pat. No. 3,940,689.

Returning to FIG. 5, the output of the 2 kHz bandpass filter 54 is rectified and is detected by means of a resettable peak detector 55. The output of the resettable peak detector 55 is fed into a sample and hold circuit 57. This sample and hold circuit 57 samples the resettable peak detector voltage just before it is to be reset to zero. This operation occurs at every negative slope zero crossing of the receiver pad voltage. An instant after the sample and hold circuit 57 goes into the hold mode, the resettable peak detector 55 is reset to zero.

The output of the 35 Hz bandpass filter 52 is fed into a fullwave rectifier 56, the output of which is fed into a resettable peak detector 58. At the negative slope zero crossing of the pad receiver voltage, the output of the resettable peak detector 58 is sampled by a sample and hold circuit 60 and reset to zero when the sample and hold 60 is in the hold mode. These events occur simultaneously with the peak detector 55 and sample and hold 57 for the 2 kHz signal.

At the occurrence of a positive slope zero crossing of the reference receiver voltage associated with the particular pad array 24 or 26, the 2 kHz eddy current sampled analog voltage and 35 Hz sampled analog voltage are each multiplexed in multiplexer circuits 61 and 63 such as the multiplexer model DG-508 made and manufactured by Siliconix Inc., Santa Clara, Calif., with the same two voltages from the other six pads in the separate array into two respective analog to digital converters 62 and 64.

The output of the 2 kHz analog to digital converter 64 is then loaded into an output buffer 66. The output of the 35 Hz analog to digital converter 62 is loaded into an intermediate buffer 68. Each receiver pad then has an amplitude word at 35 kHz matched up with its corresponding pad phase word and fed into a hard wire digital multiplier 70.

The 2 kHz signal conversion from analog to digital is sent to output buffer 66 where it is stored for transmission uphole by way of digital telemetry circuitry 100 and 102 to be described hereinbelow.

The phase word is generated by enabling a counter found in the phase difference circuitry 74 at the positive slope zero crossing of the reference receiver voltage 48 illustrated in FIG. 5 associated with a given array of receiver pads 24 or 26. One reference receiver is provided for each pad array 24 and 26 as shown in FIG. 1. The counter counts at a frequency predetermined by a clock also found in circuitry 74. The clock frequency is chosen so that if the clock is enabled for one full 35 Hz period, there is a full count in the counter. The counter stops counting whenever the negative slope zero crossing of the 35 Hz pad receiver voltage occurs. This yields a "bipolar" phase word in terms of an offset binary code, that is, zero degrees is proportional to one-half the maximum count. Before each phase word is matched up with the amplitude word in the multiplier 70, it is converted into magnitude and sign components by arithmetic circuitry 75. The magnitude part of the word is fed directly into the multiplier 70. The sign is fed past the multiplier 70 directly to circuitry 76 that alters the sign of the multiplier product. This form of the amplitude-phase product is then loaded into the output buffer 66.

Timing control circuitry 77 is provided to control the resetting of all peak detector and sample and hold circuits and to further control the multiplexing of receiver pads 30 in multiplexers 61 and 63.

Since the reference receiver phase is variable relative to the transmitter phase, and data is generated relative to the reference receiver phase, it is necessary to provide data debunching of the output data. Having done this, the data will be presented to the output at a constant rate of one complete block of data 35 times a second, regardless of the phase modulation of the reference receiver 48.

The reference receiver 48 signal is fed into a differential amplifier 78 with the same high pass filter characteristics as the receiver pad 30 differential amplifiers 51. It is then passed through a 35 Hz bandpass filter 79, fullwave rectified in a fullwave rectifier 80, and fed into a reset-table peak detector 81 which is sampled by a sample and hold circuit 82 just before it is to be reset. The reset occurs at every positive slope zero crossing of the reference receiver voltage out of the 35 Hz bandpass filter 79. The output sample and hold circuit 82 is then fed into the analog to digital converter 64 via the multiplexer 63. This conversion takes place essentially simultaneously with the conversion of the receiver pad 30 signals from the respective pad array for that reference receiver.

The phase of the reference receiver 48 is measured relative to the transmitter 22 current phase, in the same manner as the phase of the pad receiver 30 is measured relative to the reference receiver utilizing similar phase difference circuitry 83. The digital word is then fed into an intermediate buffer 84 and gated into the output buffer 66. The amplitude word of the reference receiver 48 can be used to determine if the reference receiver phase lies between 0°–360° or 360°–720°. This phase signal and/or the amplitude can be used to normalize the receiver pad signal against microscopic changes and overall/average wall thickness, magnetic properties, and variations in transmitter power. This normalization can be done downhole or uphole. In the present embodiment, it is done uphole on a computer.

The digital telemetry system 85 will then latch onto the data in the output buffer 66 and transmit it up the cable. The uphole receiver 27 illustrated in FIG. 1 will then reconstruct the data block and deformat it and display the information on the log as a function of depth.

The display consists of 24 tracks divided into groups of 12. On one side, the twelve 2 kHz eddy current amplitudes can be displayed, while on the other side, the twelve 35 kHz amplitude-phase product signals are displayed. Additional signals of interest may be displayed such as the reference receiver phase relative to the transmitter voltage, and the reference receiver amplitude for each reference receiver 48.

Figure 6:
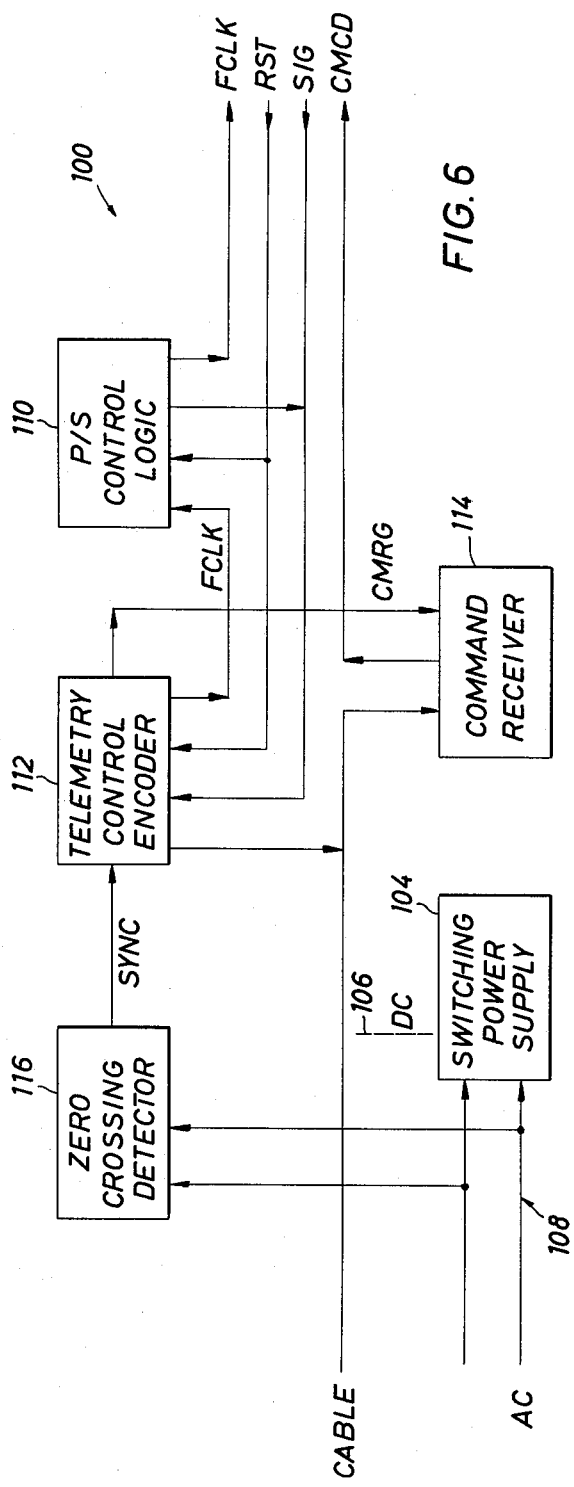
FIGS. 6–10 are block diagrams and graphical representations of signals of the digital telemetry system used to deliver the multiplied phase and amplitude signals measured by the electronic circuit of FIG. 5.
Figure 7:
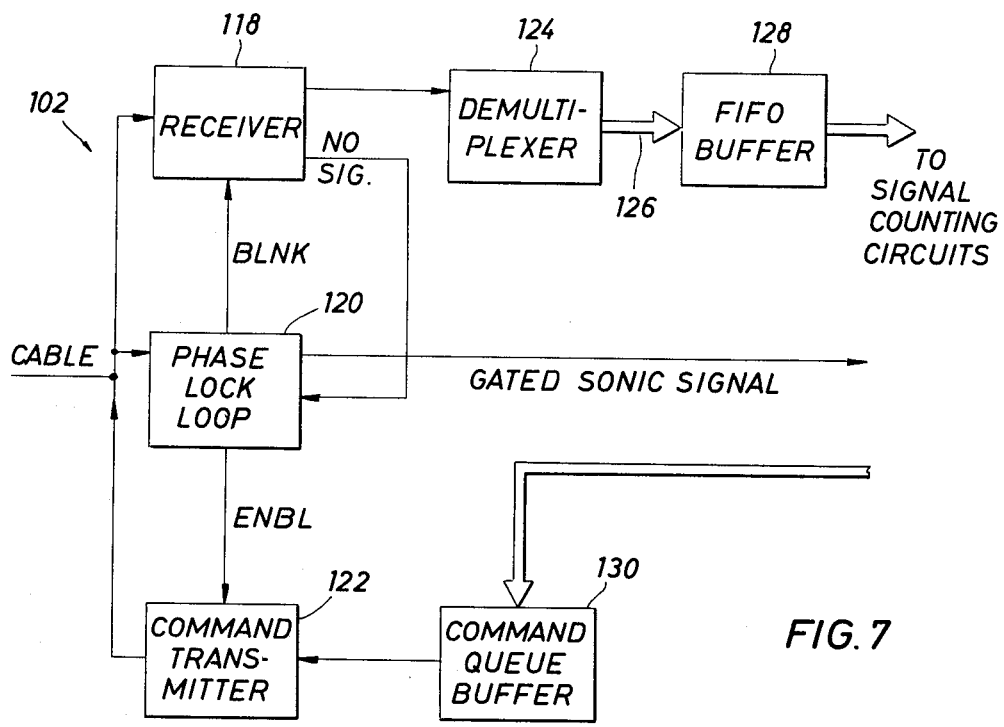

The telemetry circuits 100 and 102, utilized to send uphole the stored phase-amplitude product signal and the localized 2 kHz eddy current signal, may comprise any suitable bi-directional telemetry system. The basic components and functions of a preferred form of telemetry system are illustrated in FIGS. 6 and 7. As there depicted, the system is a word-oriented, bi-directional telemetry system having a 10 kilobit/sec upward data rate. The downhole circuits 100, illustrated in FIG. 6, include three functionally distinguishable parts: (1) the power supply, (2) the upward data circuitry, and (3) the downward data circuitry. The power supply 104 suitably comprises a switching regulator-inverter type power supply capable of accepting either d.c. or a.c. input. Where a multi-conductor cable can be used, the power supply 104 is preferably a.c. driven, indicated at 108 in FIG. 6.

Figure 8:
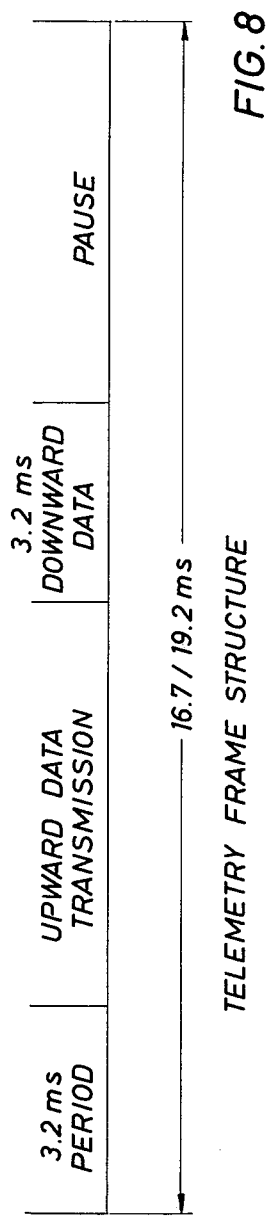

Turning briefly now to FIG. 8, the basic data structure and format of a telemetry frame will be described before proceeding further with the description of the downhole telemetry circuits 100. The initial 3.2 ms period in each frame is reserved for signals useful in other logging operations, not germane to the description of the telemetry system useful with the casing inspection tool of this invention. The 3.2 ms period is followed by the upward data from the casing inspection tool of the invention. The upward data consists of words of an odd number of bits in length. Any number of words may be sent so long as they fit in the time period provided. Following the upward data is a 3.2 ms time slot for the downward data. This is followed by a pause until the beginning of the next frame. The individual words consist of an even number of data bits (0, 2, 4, 6, 8, etc.) not exceeding 16, a parity bit and a sync condition which is two bits wide.

Returning now to FIG. 6, if one or more sensors (not shown) are included in the downhole telemetry unit, the parallel-to-serial (P/S) control logic 110 first interrogates, via the fast clock signal FCLK, the A/D converters and associated P/S converter(s) to read out the sensor data. This is done once per frame. When the last bit of sensor data has been shifted out, the P/S control logic 110 passes the clock signal FCLK along to a telemetry interface circuit (not shown). The telemetry interface circuit generates the telemetry reset signal RST upon completion of the data readout from near and far detector memories. The RST signal is applied to the P/S control logic 110 to reset the serial loop and ready it for the next frame. It also resets the telemetry control-encoder 112.

The telemetry control-encoder 112 accepts the partially encoded serial data (SIG) from the telemetry interface circuit (or from the P/S converter(s) associated with the sensors in the telemetry unit) and phase shift encodes it. The data rate is nominally 10 K bits/sec. The preferred sense of the encoding is that there will be a phase transition at each bit boundary. If the bit value is "0", no transition takes place at the center of the bit period; if the value is "1", a transition is inserted at the center of the bit period. The sync condition is a 2-bit period during which no transition takes place. The encoded signal is fed to a cable driver (not shown) which places the signal on the cable. The telemetry control-encoder 112 also includes timing circuits for generating the FCLK signal as a 20 kHz continuous square wave, and additional logic circuits for generating the 3.2 ms period for other logging operations and the gating signal CMRG for gating the command receiver 114 for reception of the downward data, also a 3.2 ms period. If no external sync is applied, as when d.c. power on a monocable is being used, the system runs free at a frame period of 19.2 ms. (See FIG. 8.) When a.c. is used to power the tool, a zero crossing detector 116 is used to produce a sync pulse at each positive crossing of the 60 Hz power waveform. The telemetry control-encoder 112 then operates the system on a 16.7 ms frame period.

Figure 9:
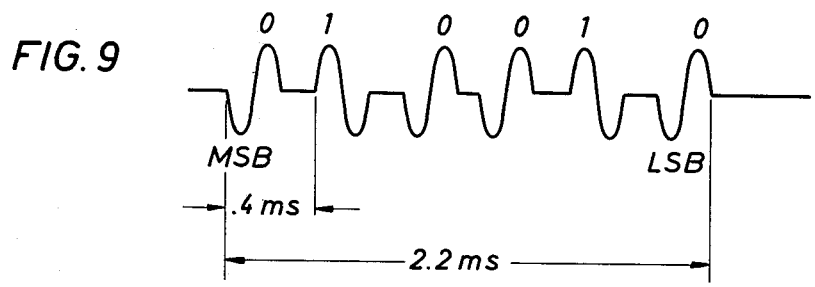
Figure 10:
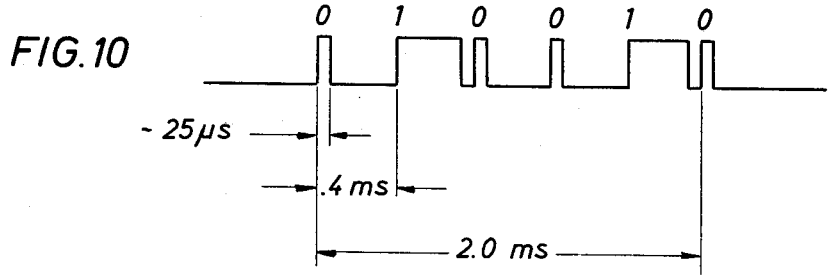

When the surface equipment senses the cessation of upward data transmission, the downward transmission is started. This data is a 6-bit word and is used to transmit commands to the tool 10. The command words are encoded as bipolar pulses with the sense that a leading negative bipolar pulse is a "0" and a leading positive pulse is a "1". The format and timing are illustrated in FIG. 9. As depicted, the most significant bit is transmitted first and the least significant bit last. The two most significant bits can then be used as tool address bits, with the four least significant bits specifying tool functions, such as change F value, plateau check, etc. In the downhole telemetry circuits 100 (FIG. 6), the CMRG signal from the telemetry control-encoder 112 is sent to the command receiver 114 at the end of the upward data transmission. In the command receiver, the downward data signal is sensed, decoded and converted into a pulse width-modulated (PWM) signal (using the code illustrated in FIG. 9) as shown in FIG. 10. This is a self-clocking signal designated the DMCD signal, and thus requires only one line.

The CMCD signal is used, for example in a command decoder circuit (not shown) in the downhole telemetry circuits 100, for use in carrying out any desired operation in the telemetry unit. For example, status checks of any sensors provided therein could be carried out.

With reference now to FIG. 7, the uphole telemetry circuits 102 may be seen to include two basic parts: (1) the upward data receiver and demultiplexer and (2) and downward (or command) data buffer and transmitter. The upward data receiver 118 amplifies and shapes the cable signal, restoring it to the shape it had when put on the cable by the downhole driver circuit. The receiver 118 also senses the cessation of the up data transmission from the downhole circuits 100. The loss of up data signal (NO SIG) is used to synchronize a phase-lock loop 120, which provides the necessary timing, via blanking signal BLNK, for gating the receiver 118 only when telemetry is expected. It also generates an enabling signal ENBL to enable the down data command transmitter 122 during the 3.2 ms down data period of each telemetry frame (see FIG. 8), as well as any required gating signals for the 3.2 ms period where other logging tools may be transmitting data.

The restored up data signal from the receiver 118 is fed to a demultiplexer 124 for conversion of the serial data into parallel data on a 16-bit wide up data bus 126. The least significant data bit of the word sent will always appear as the least significant bit in the bus 126 regardless of the length of the word sent. Parity is checked in the demultiplexer 124 and compared to the parity bit telemetered. A "parity valid" signal is included in the data bus. The data on the bus is valid until the arrival of the next telemetry word which can be as soon as 0.7 ms or as late as 1.9 ms. If desired, the up data bus 126 may also contain a 4 bit word identifier number for the purpose of allowing any data handling devices along the data bus to identify data destined for them. The words in the telemetry frame are numbered in order of appearance, with words 1 and 2 being assigned to the downhole telemetry circuits 100 for use in transmitting data acquired by any sensors included in those circuits. Each of these words may be broken up into segments, e.g. of 4 bits each, as needed to accommodate transmission of the data from the sensors.

The up data bus 126 connects to a first-in first-out buffer 128 where the count rate or other data contained in the respective words is held until transferred to count rate circuits (not shown).

Commands to the downhole tool 10 are entered through a down data bus 128. As previously mentioned, the down data commands are 6-bit words without parity. The bus 128, then, preferably has seven wires, 6 data bit lines and a busy line. A command may be entered on the bus anytime the busy line is low. The command words are queued up in a first-in first-out buffer 130 and are sent downhole one per frame. To that end, the phase lock loop 120 enables the command transmitter 122 at the end of the upward data transmission period of a frame (see FIG. 9) and a command is sent. If no commands are present in the buffer 130, a zero is sent.

While the invention has been described in detail with respect to the preferred embodiment only, that is a two transmitter device, it will be understood to those skilled in the art that other transmitter-pad array arrangements may be used to achieve similar results. For example, the transmitter-pad array arrangements shown in FIGS. 11A and 11B are alternative embodiments to the two transmitter configuration. The alternative arrangement shown in FIG. 11A in schematic form illustrates the use of a transmitter 140 disposed within a casing 142. The transmitter is located a predetermined distance between pad arrays 144 and 146. The main criterion for the distance between the transmitter 140 and the pad arrays 144 and 146 is the reduction of the effect of the direct flux coupling between the transmitter and the arrays independent of the casing wall. In the second alternative embodiment of the transmitter-pad array configuration as found in FIG. 11B, the transmitter 140 is disposed within the casing 142 a first predetermined distance from a first pad array 144 adjacent to a second pad array 146. As in the first alternative embodiment the predetermined distances are dependent upon reducing the direct mutual signal from the transmitter 140 to the pad arrays 144 and 146. The second alternative configuration however, differs from the first in that the second pad array 146 being a further distance from the transmitter 140 samples a weaker magnetic field and thus the signal from the receiver pads in the pad array 146 must be amplified with a higher gain.

Figure 11C:
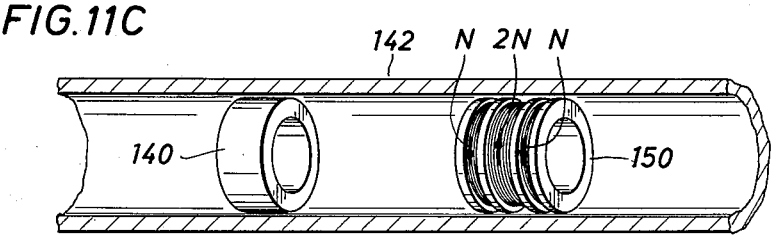
FIG. 11C illustrates a coaxial receiver coil arrangement for differentially detecting, in a single signal, the presence or absence of holes or corrosion in the casing wall.

An alternative to providing the 12 receiver coils on pads about the circumference of the tool housing by using three coaxial closely spaced coils is illustrated in FIG. 11C. The coaxial receiver coil arrangement 150 is disposed within the casing 142 a fixed distance from the transmitter 140 to differentially detect, in a single signal, the presence or absence of holes or corrosion in the casing wall adjacent to the coaxial coil 150. The three coaxial coils are electrically connected serially, so that the two end coils of N turns carry induced currents in a common direction opposite that of the 2 N turn coil.

What is claimed is:

1. Apparatus for locating and evaluating defects in ferromagnetic casing comprising:

an elongated body adapted for suspension in said casing from a well logging cable;

first means, adapted to be disposed within said casing, and located on said body, for generating an alternating magnetic field along a portion of the longitudinal axis of said casing which induces circumferential currents therein;

second means, adapted to be disposed within said casing and located on said body, said second means disposed axially from said first means, for generating at least one signal in response to perturbations of said circumferential current in said casing, said second means including:

a carrying member, a first coil having N number of windings supported by said carrying member, a second coil disposed adjacent said first coil and having 2 N number of windings serially opposed to the windings of said first coil, and a third coil disposed adjacent said second coil and having N number of windings serially opposed to the windings of said second coil; and a signal processor coupled to said second means for receiving at least one of said signals for measuring the amplitude and phase components thereof, thereby determining the characteristics of said defect.

2. Apparatus as set forth in claim 1 wherein said first means comprises at least one coaxial transmitter coil and an alternating current source driving said coaxial transmitter coil for generating an alternating magnetic field along a portion of the longitudinal axis of said casing.

3. Apparatus as set forth in claim 2 wherein said current source generates a magnetic field at a frequency in the range of 35–40 Hz.

4. Apparatus as set forth in claim 1 wherein said second means comprises first and second arrays of differential receiver coils cooperatively arranged at spaced intervals around the circumference of said body, each of said coils being operatively urged adjacent the interior wall of said casing.

5. Apparatus as set forth in claim 4 wherein said first means comprises first and second coaxial transmitter coils, and said first and second arrays of differential receivers are disposed between said first and second coaxial transmitter coils.

6. Apparatus as set forth in claim 4 wherein said first and second arrays of differential receiver coils are adapted to be disposed in said casing on opposite sides of said first means, said first and second arrays located a predetermined distance from said first means.

7. Apparatus as set forth in claim 4 wherein said first and second arrays of differential receivers are adapted to be disposed within said casing a predetermined distance from said first means, and are located in adjacent relationship to one another.

8. Apparatus as set forth in claim 4 wherein each of said first and second arrays of differential receiver coils comprise a plurality of receiver coils in angular spaced relationship to one another.

9. Apparatus as set forth in claim 4 wherein each of said first and second arrays comprise six differential receiver coils angularly spaced 30° apart.

10. Apparatus as set forth in claim 1 wherein said first, second and third coils are disposed on said carrying member in closely spaced coaxial relationship along the longitudinal axis of said casing.

11. An apparatus as set forth in claim 1 wherein said signal processor includes means for measuring said amplitude component comprising:
first amplification means electrically connected to said second means for generating an amplified signal;
first filter means electrically connected to said first amplification means for screening said amplified signal for any noise component;
means electrically connected to said first filter means for rectifying said amplified signal to retain only a predetermined portion of said amplified signal; and,
detector means electrically connected to said rectifying means for generating a rectified maximum amplitude signal.

12. Apparatus as set forth in claim 11 further including a third means adapted to be disposed in the center of said casing in adjacent relationship to said second means for providing a reference signal indicative of the phase of said magnetic field.

13. An apparatus as set forth in claim 12 wherein said signal processor further includes means for measuring said phase component of said signal comprising:
second amplification means electrically connected to said third means for amplifying said reference signal;
second filtering means electrically connected to said second amplification means for screening noise from said amplified reference signal;
a first zero crossing pulse network, electrically connected to said first filtering means, for determining the phase of said signal;
a second zero crossing pulse network, electrically connected to said second filtering means, for determining the phase of said reference signal; and
means electrically connected to said first zero crossing pulse network and said second zero crossing pulse network, for generating a phase difference signal representing the phase difference between said signal and said reference signal.

14. Apparatus as set forth in claim 13 further including multiplication means for generating a signal which is the product of said amplitude signal and said phase difference signal.

15. Apparatus as set forth in claim 1 further including fourth means operatively associated with said second means and adapted to be disposed within said carrying member in concentric relationship with said first, second and third coils and parallel to said casing wall, for locating defects on the interior wall of said casing.

16. Apparatus as set forth in claim 15 wherein said fourth means comprises an oscillator coil for inducing high frequency localized eddy currents in said casing wall.

17. Apparatus as set forth in claim 15 wherein said oscillator coil generates a magnetic field at a frequency of 2 kHz.

18. Apparatus for locating and evaluating defects in ferromagnetic casing comprising:
an elongated body adapted for suspension in said casing from a well-logging cable;
at least one coaxial transmitter coil adapted to be positioned within said casing on said body, for generating an alternating magnetic field along a portion of the longitudinal axis thereby inducing circumferential currents in said casing; and
at least one array of differential receiver coils located on said body and adapted to be disposed within said casing in spaced axial relationship to said coaxial transmitter coil, for generating a signal in response to perturbations of said circumferential currents in said casing, wherein each of said differential receiver coils includes:
a carrying member;
a first coil having N number of windings supported by said carrying member;
a second coil disposed adjacent said first coil having 2N number of windings serially opposed to said windings of said first coil; and
a third coil disposed adjacent said second coil having N number of windings serially opposed to said windings of said second coil.

19. Apparatus for locating and evaluating defects in ferromagnetic oil well bore casing comprising:
an elongated body adapted for suspension in said casing from a well-logging cable;
at least one coaxial transmitter coil located on said body and adapted to be positioned within said casing, driven by an alternating current source, for generating an alternating magnetic field, said magnetic field inducing circumferential currents in said casing; and
first and second arrays of differential receiver coils located on said body and adapted to be disposed within said casing in spaced axial relationship to said coaxial transmitter coil, for generating at least one signal in response to perturbations in said circumferential currents, each of said differential receiver coils are enclosed in a receiver pad and include:

a carrying member;

a first coil having N number of windings disposed within said carrying member;

a second coil disposed adjacent said first coil having 2N number of windings serially opposed to said windings of said first coil; and a third coil disposed adjacent said second coil having N number of windings serially opposed to said windings of said second coil.

20. Apparatus for locating and evaluating defects in ferromagnetic casing comprising:

an elongated body adapted for suspension in said casing from a well-logging cable;

first means, adapted to be disposed within said casing, and located on said body, for generating an alternating magnetic field along a portion of the longitudinal axis of said casing which induces circumferential currents therein;

second means, adapted to be disposed within said casing and located on said body, said second means in spaced axial relationship with said first means, for generating at least one signal in response to perturbations of said circumferential currents in said casing, said second means including a carrying member, and three coils disposed thereon, said coils located in adjacent relationship to one another and having N, 2N, and N number of windings respectively, said coils electrically connected in a serial manner forming a differential coil pair.

21. A method of distinguishing actual defects in ferromagnetic casing from magnetic anomalies comprising the steps of:

generating a first alternating magnetic field in the casing thereby inducing circumferential currents in said casing;

receiving a measured phase signal from a differential receiver coil arrangement in close proximity to said casing wall, said differential receiver coil arrangement being spaced axially from the source of said first alternating magnetic field;

receiving a phase reference signal from a reference coaxial coil disposed axially from said source of first alternating magnetic field;

generating a phase difference signal between said measured phase signal and said reference phase signal; and identifying actual defects from the shape of said phase difference signal, where a phase change from substantially 0° toward −90° and then through 0° toward +90° and then through 0° degrees toward −90° and back to substantially 0° indicates a real defect, and where the phase difference signal changes from substantially 0° degrees toward −90° and then back toward substantially 0° indicates a magnetic anomaly.

22. The method of claim 21 further including the step of receiving a measured amplitude signal and identyfing the size of said defect in proportion to the amplitude of said amplitude signal.

23. A method as set forth in claim 21 further including the steps of generating a second magnetic field at a frequency higher than said first magnetic field and inducing localized eddy currents in said casing in a plane 90° from said circumferential currents induced by said first magnetic field; detecting perturbations in said localized eddy currents; and generating a second signal in response thereto.

24. A method according to claim 23 and further including the step of measuring the amplitude of said second signal.

25. A receiver coil arrangement for detecting defects in ferromagnetic oil well casing comprising:

a non-conductive carrying member;

first, second and third multiple turn conductive coils disposed on said carrying member having N, 2N, and N number of windings respectively, said coils in adjacent relationship to one another, with each of said coils wound in the same direction and electrically connected in series such that an induced current circulating in said coil having 2N turns flows in a direction opposite to induced currents flowing in said coils having N turns.

26. The receiver coil arrangement of claim 24 wherein said non-conductive carrying member is a fiberglass-expoxy composite bobbin.

27. The receiver coil arrangement of claim 24 wherein each of said coils has at least fifteen hundred windings.

28. The receiver coil arrangement of claim 24 wherein said first, second and third multiple turn conductive coils disposed on said non-conductive carrying member are enclosed in a receiver pad.

29. The receiver coil arrangement of claim 24 wherein said first, second and third multiple turn conductive coils are disposed on said non-conductive carrying member in closely spaced coaxial relationship.

30. A receiver coil arrangement for detecting defects in ferromagnetic oil well casings comprising:

a non-conductive carrying member;

a first coil having N number of windings supported by said carrying member;

a second coil disposed adjacent said first coil and having 2N number of windings serially opposed to the windings of said first coil; and a third coil disposed adjacent said second coil and having N number of windings serially opposed to the windings of said second coil.

31. A method of distinguishing actual defects in ferromagnetic casing from magnetic anomalies comprising the steps of:

generating a first alternating magnetic field in the casing thereby inducing circumferential currents in said casing;

receiving a measured phase signal from a differential receiver coil arrangement in close proximity to said casing wall, said differential receiver coil arrangement being spaced axially from the source of said first alternating magnetic field;

receiving a phase reference signal from a reference coaxial coil disposed axially from said source of first alternating magnetic field;

generating a phase difference signal between said measured phase signal and said reference phase signal; and identifying actual defects from the shape of said phase difference signal, where one unidirectional phase pulse indicates a magnetic anomaly, and where at least two pulses of opposite polarity indicates a real defect.

32. A method of distinguishing actual defects in ferromagnetic casing from magnetic anomalies comprising the steps of:

generating a first alternating magnetic field in the casing thereby inducing circumferential currents in said casing;

receiving a measured phase signal from a differential receiver coil arrangement in close proximity to said casing wall, said differential receiver coil arrangement being spaced axially from the source of said first alternating magnetic field;

receiving a phase reference signal from a reference coaxial coil disposed axially from said source of first alternating magnetic field;

generating a phase difference signal between said measured phase signal and said reference phase signal;

receiving a measured amplitude signal from said differential receiver coil arrangement;

multiplying said amplitude signal by said phase difference signal to generate an identification signal; and identifying actual defects from the shape of said phase difference signal, where a phase change from substantially 0° toward −90° and then through 0° toward +90° and then through 0° toward −90° and back to substantially 0° indicates a real defect, and where the phase difference signal changes from substantially 0° toward −90° and then back toward substantially 0° indicates a magnetic anomaly.

* * * * *

Disclaimer 4,292,589.—*Stephen D. Bonner*, Houston, Tex. EDDY CURRENT METHOD AND APPARATUS FOR INSPECTING FERROMAGNETIC TUBULAR MEMBERS. Patent dated Sept. 29, 1981. Disclaimer filed Apr. 9, 1986, by the assignee, *Schlumberger Technology Corp.*

Hereby enters this disclaimer to claims 26, 27, 28, 29, 30 and 31 of said patent.

[*Official Gazette June 17, 1986.*]